US012686748B2

(12) United States Patent
Litvinov

(10) Patent No.: US 12,686,748 B2
(45) Date of Patent: Jul. 21, 2026

(54) METHOD FOR MINERALISING A BIOPOLYMER MEMBRANE AND MEMBRANES THEREBY OBTAINED

(71) Applicant: REGESKA, Lyons (FR)

(72) Inventor: Sergei Litvinov, Samara (RU)

(73) Assignee: REGESKA, Lyons (FR)

( * ) Notice: Subject to any disclaimer, the term of this patent is extended or adjusted under 35 U.S.C. 154(b) by 1082 days.

(21) Appl. No.: 17/766,377

(22) PCT Filed: Oct. 9, 2020

(86) PCT No.: PCT/FR2020/051783
§ 371 (c)(1),
(2) Date: Apr. 4, 2022

(87) PCT Pub. No.: WO2021/069846
PCT Pub. Date: Apr. 15, 2021

(65) Prior Publication Data
US 2024/0059854 A1 Feb. 22, 2024

(30) Foreign Application Priority Data

Oct. 10, 2019 (FR) ...................................... 1911259

(51) Int. Cl.
*C08J 7/12* (2006.01)
*A61K 9/14* (2006.01)
(Continued)

(52) U.S. Cl.
CPC ................... *C08J 7/12* (2013.01); *A61K 9/14* (2013.01); *A61K 38/39* (2013.01); *C08J 5/18* (2013.01); *C08J 2389/04* (2013.01)

(58) Field of Classification Search
None
See application file for complete search history.

(56) References Cited

U.S. PATENT DOCUMENTS 5,532,217 A 7/1996 Silver et al.
5,739,286 A 4/1998 Silver et al.
(Continued)

FOREIGN PATENT DOCUMENTS

EP 3181158 A1 12/2015
EP 3021883 B1 11/2016
(Continued)

OTHER PUBLICATIONS

Rhee et al., "Hydroxyapatite Coating on a Collagen Membrane by a Biomimetic Method," Journal of American Ceramic Society, vol. 81(11), pp. 3029-3031 (1998). (Year: 1998).*
(Continued)

*Primary Examiner* — Ha S Nguyen
(74) *Attorney, Agent, or Firm* — Arrigo, Lee, Guttman & Mouta-Bellum LLP

(57) ABSTRACT

The present invention relates to a method for mineralising a biopolymer membrane, comprising the following steps:
  a) Introduction of an assembly (3) constituted of a bio-polymer membrane (4) comprised between two cellu-lose sheets (A) and (B), in a vessel comprising:
    a first compartment (1) and a second compartment (2), each comprising an electrode, a first electrode being an anode placed in the first compartment (1) and a second electrode being a cathode placed in the second compartment (2),
    the walls of the first compartment (1) and the second compartment (2) brought into contact with one another each having an opening placing in commu-nication the first and the second compartments,
  the assembly (3) being arranged in said opening between the first and the second compartments in such a way as to close it, the cellulose sheet (A) being on the side of
    (Continued)

the first compartment (1) and the cellulose sheet (B) on the side of the second compartment (2), b) filling the first compartment (1) with an aqueous solution containing at least one cation chosen from: calcium ions, silver ions, zinc ions, copper ions, sodium ions, magnesium ions and aluminium ions, and the second compartment (2) with an aqueous solution containing at least one anion chosen from fluoride ions, sulphate ions, carbonate ions, silicate ions and phosphate ions;

c) application of an electrical voltage between the electrodes;

d) turning over the assembly (3) in such a way that the cellulose sheet (A) is on the side of the second compartment and the cellulose sheet (B) on the side of the first compartment, or exchange of the solutions and electrodes of the first and the second compartments;

c') application of an electrical voltage between the electrodes, said voltage being equal to that applied at step (c) and being applied for a duration identical to that of step (c);

e) removal and rinsing of the assembly (3);

f) recovery and drying of the mineralised biopolymer membrane.

20 Claims, 7 Drawing Sheets

(51) Int. Cl.

| | |
|---|---|
| *A61K 38/39* | (2006.01) |
| *A61L 31/04* | (2006.01) |
| *A61L 31/08* | (2006.01) |
| *C08J 5/18* | (2006.01) |

(56) References Cited

U.S. PATENT DOCUMENTS

| | | | |
|---|---|---|---|
| 6,395,036 | B1 | 5/2002 | Czernuszka et al. |
| 6,589,590 | B2 | 7/2003 | Czernuszka et al. |

FOREIGN PATENT DOCUMENTS

| | | | |
|---|---|---|---|
| RU | 2174848 | C1 | 10/2001 |
| RU | 2410040 | C1 * | 1/2011 |
| WO | 2008/096334 | A2 | 8/2008 |
| WO | 2013/111077 | A1 | 8/2013 |
| WO | 2013/190534 | A2 | 12/2013 |

OTHER PUBLICATIONS

Cai et al., "Preparation of biomimetic hydroxyapatite by biomineralizaton and calcination using poly(L-lactide)/gelatin composite fibrous mat as template," Material Letters, vol. 91, pp. 275-278 (2013). (Year: 2013).*

Jie et al., "Hydroxyapatite Nucleation and Growth on Collagen Electrospun Fibers Controlled with Different Mineralization Conditions and Phosvitin," Macromolecular Research, vol. 25, pp. 905-912 (2017) (Year: 2017).*

Oxford English Dictionary, "Alveolar," https://www.oed.com/dictionary/alveolar_adj, accessed on Dec. 2, 2025. (hereinafter Oxford-Aveolar). (Year: 2025).*

Oxford English Dictionary, "Alveolus," https://www.oed.com/dictionary/alveolus_n, accessed on Dec. 2, 2025. (hereinafter Oxford-Aveolar). (Year: 2025).*

Antoine Boyer, Synthesis, characterisation and biological evaluation of carbo-silicate calcium phosphate apatites. Biotechnologies. Ecole Nationale Supérieure des Mines de Saint-Etienne, 2014. 1-225.

Zou et al. Biomimetic mineralization on natural and synthetic polymers to prepare hybrid scaffolds for bone tissue engineering, Colloids and Surfaces B: Biointerfaces, 2019, 178, 222-229.

* cited by examiner

Figure 4

METHOD FOR MINERALISING A BIOPOLYMER MEMBRANE AND MEMBRANES THEREBY OBTAINED

FIELD OF THE INVENTION

The present invention relates to the field of tissue engineering, that is to say the manufacture of synthetic biocompatible organic tissues, being able to be implanted in living organisms.

More specifically, the present invention relates to a method for preparing a biomaterial for use in human surgery and medicine. This biomaterial consists in a biopolymer membrane covered with nanocrystals of mineral compounds, having a particular structure. This biopolymer membrane may notably be covered with nanocrystals of calcium phosphate compounds, notably chosen from hydroxyapatite or brushite.

PRIOR ART

In medicine, the implantation of biopolymer structures in living organisms is a conventional technique, used to promote the reconstruction of biological tissue, notably the reconstruction of bone tissue.

These biopolymer structures, used as bone substitutes, are composed of natural fibres (in the form of films, fibres, compact and/or porous structures) often associated with active compounds to improve their biocompatibility: cells, hormones and/or growth factors, or minerals.

These bone substitutes must enable osteoconduction, which designates the capacity of the biomaterial to serve as passive support to bone regrowth. The biomaterial must further be porous and resorbable. The porosity of the biomaterial enables the implant to vascularise and to resorb progressively. The rate of resorption of the biomaterial must correspond to the needs of the bone neoformation: not too quickly, so that it can serve as support for bone formation; not too slowly, to limit the risks of infection and so as not to impair the growth of the bone by mechanical hindrance.

Several types of biomaterials are used as passive support for cellular and tissular colonisation: they may be natural or synthetic ceramics, or different materials of natural origin, the chemical composition of which is close to that of the mineral phase of bone.

The synthetic biomaterials the most often used for filling bone defects are hydroxyapatite and tricalcium phosphates, two mineral species of the phosphates family, pure or in mixtures.

The combination of biopolymer and nanocrystalline hydroxyapatite, such as collagen and hydroxyapatite, is known and has been used as bone substitute since the 1990s (see for example U.S. Pat. Nos. 5,231,169, 6,201,039, EP0747067).

Numerous therapeutic applications of this biomaterial have been proposed, for example:

The patent application EP 3181158 is relative to a nanoporous biomaterial, comprising hydroxyapatite deposited or precipitated on a gel of biodegradable polymer, notably chosen from collagen and alginate. This biomaterial may be used in orthopaedics, for dental surgery and for reconstructive surgery.

The international patent application WO 2008/096334 describes an implant intended to repair cartilage damage, comprising a backbone composed of collagen and hydroxyapatite.

The patent application RU2410040 describes a prothesis composed of a collagen or alginate membrane, covered with hydroxyapatite crystals, intended for the surgical treatment of urinary incontinence in women.

The international patent application WO 2013/111077 describes a composition comprising, among others, sodium alginate and hydroxyapatite, for the treatment of gastro-intestinal ailments.

The international patent application WO 2013/190534 describes a compactable composite powder comprising a composition of silicate, collagen and calcium phosphate. This powder may be obtained by grinding a material composed of mineralised collagen, and may be used as implant. Several methods for mineralising biopolymer membranes have been described. Conventional techniques consist in firing minerals at very high temperatures, such as ceramic, which leads to extremely hard crystals.

"Gentler" techniques have also been proposed:

The U.S. Pat. No. 6,395,036 describes a method for preparing a composite material, where calcium ions and phosphate ions circulate around a collagen membrane and precipitate, when they encounter each other, into hydroxyapatite crystals.

The international patent application WO 2008/096334 describes a method for preparing a collagen scaffold, covered with hydroxyapatite crystals, by lyophilisation and gel.

The patent EP 3021883 describes a composite material comprising a backbone of collagen fibres, at least partially coated with hydroxyapatite crystals with epitactic growth. The method for obtaining said material comprises the immersion of fibrous collagen in an aqueous solution saturated with calcium and phosphate ions ($Ca2+/HxPO4(3-x)$), nanocrystals of hydroxyapatite forming on the collagen fibres, the method being stopped by removing the collagen from the solution, and rinsing.

The patent RU2174848 describes a method for preparing a mineralised collagen membrane, comprising the use of electrodes to circulate ions by electrophoresis. Under the action of this electrical current, the solution containing calcium acidifies, thereby creating hydrogen ions capable of dissolving the hydroxyapatite crystals formed. The solution proposed is to stabilise the pH of the solutions at 11 for the solution of calcium ions, and at a value of 10.5 to 11 for that containing phosphate ions, by adding calcium hydroxide continually to the solution containing the calcium ions.

The U.S. Pat. Nos. 5,532,217, 5,739,286 are relative to a method for mineralising collagen fibres, in which the collagen fibres are inserted into a vessel comprising two tanks, one containing calcium chloride, and the other potassium phosphate. The two vessels are separated by a tube constituted of cellulose dialysis membranes, into which the collagen fibres are inserted. The pH of the solutions are adjusted in such a way that the ions precipitate, by forming nanocrystals on the collagen. The procedure, relatively slow, lasts 7 days.

The U.S. Pat. No. 6,589,590 describes a method for mineralising a biopolymer, comprising bringing a biopolymer membrane into contact with, on the one side a solution containing calcium ions, and on the other side a solution containing phosphate ions; the ions diffusing through the biopolymer membrane precipitate into hydroxyapatite crystals when they encounter one another.

The present invention is relative to a novel method for "gently" mineralising a biopolymer membrane, implementing an original combination of different methods in order to obtain nanocrystals of minerals on said membrane. This mineralised membrane has interesting novel characteristics. Indeed, the crystals formed are in a state of low crystallinity and with particular structural qualities. The mineralised membrane has rapid resorption (between 5 and 60 days, and in particular in less than 30 days, in less than 25 days, or even less than 21 days) after implantation in a living organism, and has positive biological effects (anti-oxidant, anti-inflammatory) as of implantation in the organism, or after administration of a powder prepared from this mineralised membrane.

The novel properties of these mineralised biopolymer membranes are such that novel therapeutic applications may be envisaged, in addition to the treatment of bone and cartilage disorders.

DESCRIPTION OF THE INVENTION

The present invention relates to a method for mineralising a biopolymer membrane, comprising the following steps:

a) Introduction of an assembly (3) constituted of a biopolymer membrane (4) comprised between two cellulose sheets (A) and (B), in a vessel comprising:

a first compartment (1) and a second compartment (2), each comprising an electrode, a first electrode being an anode placed in the first compartment (1) and a second electrode being a cathode placed in the second compartment (2), the walls of the first compartment (1) and the second compartment (2) brought into contact with one another each having an opening placing in communication the first and the second compartments, the assembly (3) being arranged in said opening between the first and the second compartments in such a way as to close it, the cellulose sheet (A) being on the side of the first compartment (1) and the cellulose sheet (B) on the side of the second compartment (2), b) filling the first compartment (1) with an aqueous solution containing at least one cation chosen from: calcium ions, silver ions, zinc ions, copper ions, sodium ions, magnesium ions and aluminium ions, and the second compartment (2) with an aqueous solution containing at least one anion chosen from fluoride ions, sulphate ions, carbonate ions, silicate ions and phosphate ions;

c) application of an electrical voltage between the electrodes;

d) turning over the assembly (3) in such a way that the cellulose sheet (A) is on the side of the second compartment and the cellulose sheet (B) on the side of the first compartment, or exchange of the solutions and electrodes of the first and the second compartments;

c') application of an electrical voltage between the electrodes, said voltage being equal to that applied at step (c) and being applied for a duration identical to that of step (c);

e) removal and rinsing of the assembly (3);

f) recovery and drying of the mineralised biopolymer membrane.

The present invention also relates to a biopolymer membrane mineralised on its two faces, susceptible to be obtained by the method described above.

The present invention also relates to a biopolymer membrane mineralised on its two faces with nanocrystals of calcium phosphate organised in the form of platelets and spherical nanoporous crystals having an alveolar structure.

Another subject matter of the invention is a powder constituted of a mineralised biopolymer membrane such as described above, reduced into powder.

Another subject matter of the invention is a solution comprising said powder in suspension in a pharmaceutically acceptable vehicle.

The present invention also relates to a mineralised biopolymer membrane such as described, or a powder such as described, or a solution such as described, for the therapeutic use thereof in the treatment of bone, cartilage, pancreatic, renal, urethral, urethral, and vesical, testicular, ovarian, intestinal, hepatic, neurological, cardiac, tympanic, ocular, urinary, gynaecological, pulmonary, bronchial, tracheal, vascular, conjunctive, cutaneous, mucosal, dental, gingival and/or haematopoietic tissue and immune disorders.

DESCRIPTION OF THE FIGURES

FIG. 1 represent a cross-section of a vessel comprising a first compartment (1) and a second compartment (2), each comprising an electrode, the anode being placed in the first compartment (1) and the cathode in the second compartment (2), and an assembly (3) arranged in the opening between the first and the second compartments in such a way as to close it. This assembly is constituted of a biopolymer membrane (4) surrounded by two cellulose sheets, cellulose sheet (A) being on the side of the first compartment (1) and cellulose sheet (B) on the side of the second compartment, during step (c).

FIG. 2 represents the same device as FIG. 1 but during step (c'), the assembly (3) having been turned over in such a way that cellulose sheet (A) is on the side of the second compartment (2) and cellulose sheet (B) on the side of the first compartment (1).

FIG. 3 represents the variation in total antioxidant capacity measured in the urine of an individual (67 year old male in good health) to whom has been administered a powder according to the invention. The total antioxidant capacity (TAC) is expressed in percentage compared to the control values, as a function of the number of days of administration (on the X-axis).

FIG. 4. Photos of the crystals present on the membranes, by Zeiss Supra 55VP scanning electron microscopy (SEM), on the two faces of the mineralised collagen membranes. Samples 7, 4, 6 and 5 have been photographed with the following enlargements (from left to right): ×250, ×750, ×2000, ×10.000, ×20.000 and ×30.000.

On the very left, a photo without enlargement shows the appearance of the mineralised membrane. Sample 5 corresponds to the membrane obtained by the method according to the invention.

Figure 5:
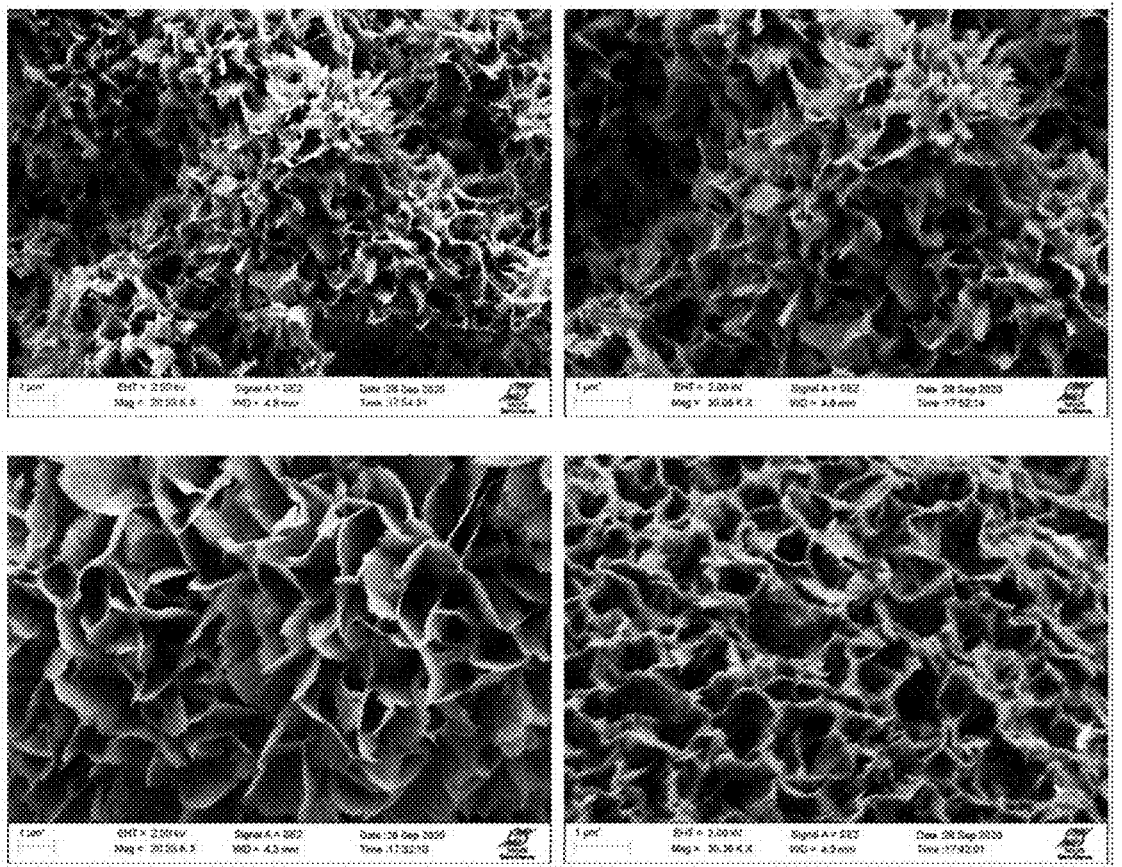

FIG. 5. Photos of the crystals present on the membrane of sample 5, by Zeiss Supra 55VP scanning electron microscopy (SEM), at the following enlargements: ×20.000 and ×30.000. Face 1 is above, face 2 below.

Figure 6:
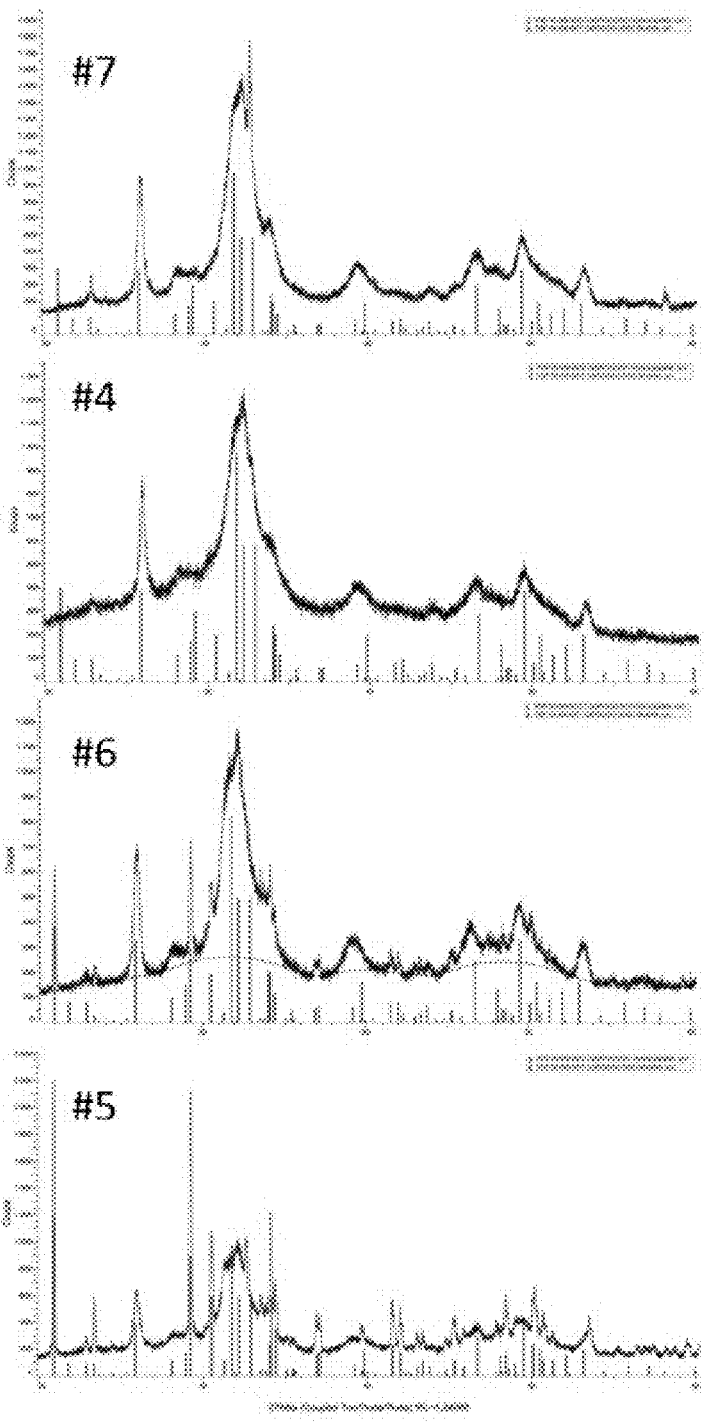

FIG. 6: Diffractograms of matrices of mineralised collagen. Comparison of the diffraction spectra obtained on samples 7, 4, 6 and 5 ground manually.

Figure 7:
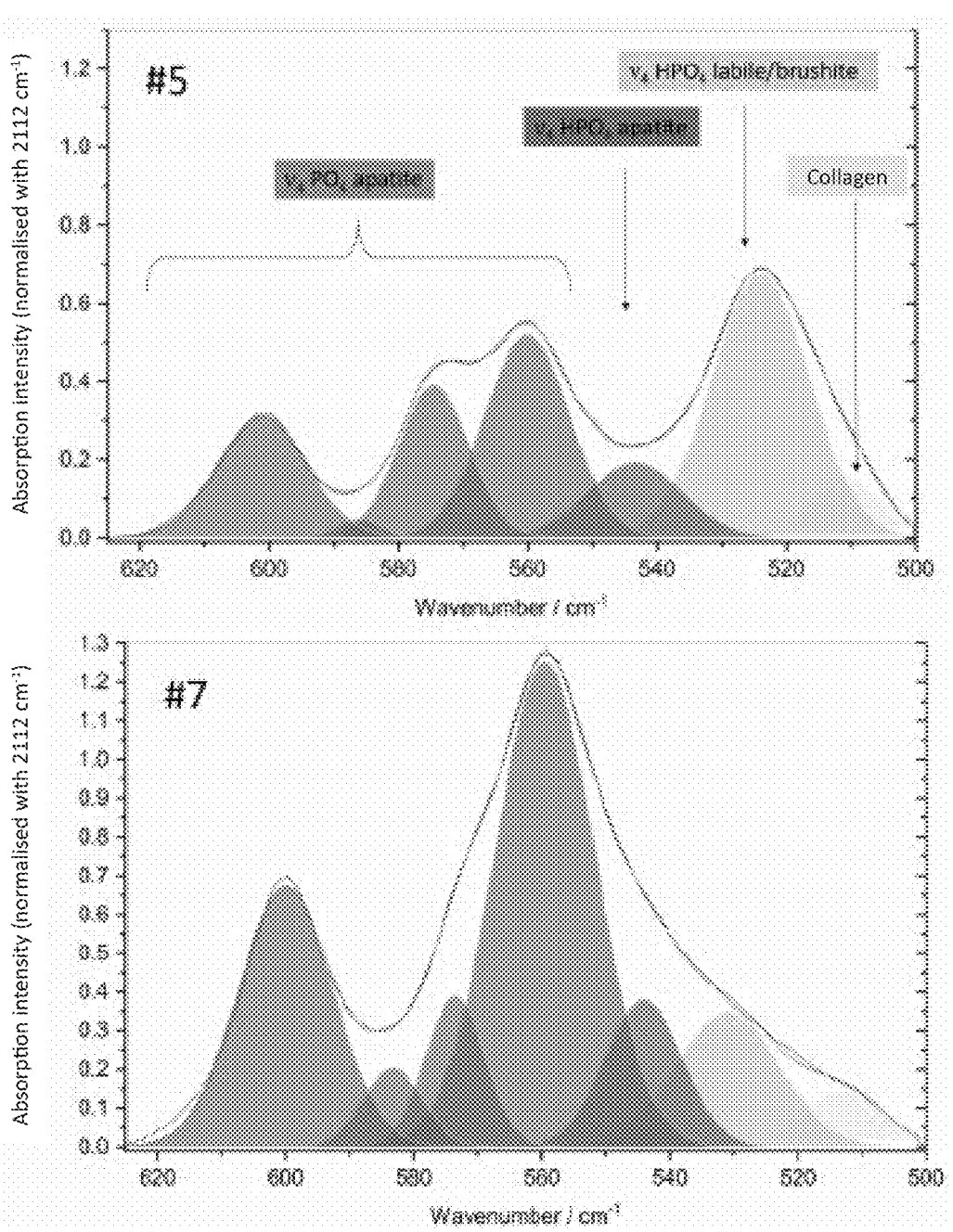

FIG. 7. Curve fitting in the $HPO_4$ domain on normalised IR spectra. Comparison of bands relative to $PO_4$ and apatitic $HPO_4$ and labile $HPO_4$ groups on samples 5 (top) and 7 (bottom) ground manually.

DETAILED DESCRIPTION OF THE INVENTION

The present invention relates to a method for mineralising a biopolymer membrane, making it possible to obtain nanocrystals of a particular type on this membrane. The membrane has the advantage of rapid resorption after implantation in a living organism, and has positive biological effects as of its implantation in the organism, or following administration of a powder obtained from said membrane.

Biopolymer Membrane

A membrane designates in common language a flexible wall. Each membrane has a specific rigidity and porosity.

A polymer is a macromolecule constituted of an assembly of numerous monomeric units. A biopolymer designates a natural polymer, directly produced by living beings (plants, algae, animals, mushrooms, etc.) or derived directly from a natural product. They are compounds of amino acids, sugars, nucleotides or other monomeric organic compounds. Biopolymers of plant origin and those of animal original are distinguished.

Among biopolymers of plant origin, cellulose, starch, and alginate (produced by seaweed) may notably be cited.

Among biopolymers of animal origin, collagen and chitosan may notably be cited, derived from the treatment of chitin produced by crustacea.

According to a preferred embodiment of the invention, the biopolymer membrane is a collagen, alginate or chitosan membrane.

According to a first embodiment, the membrane is constituted of collagen.

Collagen is a protein macromolecule, constituted of three associated alpha polypeptide chains, constituted of amino acids. These chains are linked together by hydrogen bonds between hydroxylysine and hydroxyproline and by covalent bonds. The macromolecule is usually organised in the form of fibres. Several types of association of polypeptide chains and configuration are possible; thus, several types of collagen exist, designated type I, type II, type II, etc. Collagen is present in the extracellular matrix of animal cells, and confers on tissues mechanical resistance to stretching. Collagen is very little allergenic, and is used in numerous therapeutic applications.

According to a second embodiment, the membrane is constituted of alginate.

Alginate is a polysaccharide produced by seaweed. It is a polymer formed of two monomers: mannuronate or mannuronic acid, certain units of which are acetylated, and guluronate or guluronic acid. The proportion and the distribution of these two monomers vary: several types of alginates thus exist, having variable chemical and physical properties. In medicine, alginate is used to encapsulate fragile medicines or biological substances. Alginate may also be used in the confection of certain dressings. It is also the product used by dentists to take dental impressions.

According to a third embodiment, the membrane is constituted of chitosan.

Chitosan is a polysaccharide composed of the random distribution of ß-(1-4) linked D-glucosamine (de-acetylated unit) and N-acetyl-D-glucosamine (acetylated unit). It is produced by chemical deacetylation in alkaline or enzymatic medium of chitin, the component of the exoskeletons of arthropods, the endoskeletons of cephalopods, or the walls of mushrooms. Chitosan is widely used in cosmetic and dietary products. In medicine, chitosan may be used as biomaterial, notably for tissue regeneration, haemostasis and osteogenesis.

The shape of the biopolymer membrane will be for example a parallelepiped, such as a square, a rectangle or a lozenge.

The size of the biopolymer membrane will be chosen by those skilled in the art, as a function of the envisaged applications; it could for example be of a size of around 10 $cm^2$, or 20 $cm^2$, or 100 $cm^2$ (square of 10*10 cm). It could also have much more ample measurements, for example be of a size of 1 $m^2$, 10 $m^2$ or even 100 $m^2$.

Assembly

For the method for mineralising a biopolymer membrane according to the invention, said membrane is arranged inside an assembly constituted of two identical cellulose sheets, designated (A) and (B) to distinguish their emplacement vis-à-vis two compartments containing distinct aqueous solutions.

This assembly is placed between the two compartments (1) and (2), in such a way as to separate them hermetically: the only encounter surface of the two solutions placed in each of the compartments (1) and (2) being this assembly.

The cellulose sheets (A) and (B) used are identical. They are of size slightly greater than that of the biopolymer membrane, in order to ensure leak tightness between the compartment (1) and the compartment (2). Their thickness is preferably 0.02 mm to 0.03 mm. They could notably be cellophane sheets.

Mineralisation of the Membranes: Ionic Solutions Used

During step (b) of the method according to the invention, the first and the second compartments are filled with the following aqueous solutions:

in the first compartment (1), an aqueous solution containing at least one cation chosen from: calcium ions, silver ions, zinc ions, copper ions, sodium ions, magnesium ions and aluminium ions, and in the second compartment (2), an aqueous solution containing at least one anion chosen from fluoride ions, sulphate ions, carbonate ions, silicate ions and phosphate ions.

For example, the following solutions could be employed for the implementation of the invention:

TABLE 1

| Solutions and/or cation(s) present in the solution of compartment (1) | Solutions and/or anion(s) present in the solution of compartment (2) | Crystals formed on the biopolymer membrane |
|---|---|---|
| Calcium chloride $Ca(Cl)_2$ | Ammonium phosphate $NH_4H_2PO_4$ $(NH_4)_2HPO_4$ $(NH_4)_3PO_4$ | Hydroxyapatite $Ca_5(PO_4)_3(OH)$ |
| Calcium chloride $Ca(Cl)_2$, with the addition of silver ions ($Arg^{2+}$), and/or zinc ions ($Zn^{2+}$) and/or copper ions ($Cu^+$ or $Cu^{2+}$) | Ammonium phosphate $NH_4H_2PO_4$ $(NH_4)_2HPO_4$ $(NH_4)_3PO_4$, optionally with the addition of silicate ions $(SiO_4)^{4-}$ | Hydroxyapatite substituted with silver, zinc, copper, and/or silicate ions |
| Magnesium ions $Mg^{2+}$ | Sulphate ions $SO_4^{2-}$ | Magnesium sulphate $MgSO_4$ |
| Aluminium ions $Al^{3+}$ | Sulphate ions $SO_4^2$ | Aluminium sulphate $Al_2(SO_4)_3$ |

According to a preferred embodiment of the invention, the aqueous solution placed in the first compartment (1) contains at least calcium ions, and the aqueous solution placed in the second compartment (2) contains at least phosphate ions.

According to another preferred embodiment of the invention, the aqueous solution placed in the first compartment (1) contains as cations only calcium ions, and the aqueous solution placed in the second compartment (2) contains as anions only phosphate ions, in addition to the presence of ions derived from the decomposition of water.

Preferentially, they will be the following solutions:

calcium chloride Ca(Cl)$_2$ with the addition of calcium hydroxide Ca(OH)$_2$, and ammonium phosphate, with one, two or three solutions of substituted ammonium phosphate, with the addition of a solution of ammonia solution (NH$_3$) concentrated to 25% by weight.

It is understood that these solutions could comprise, apart from the ions specified above, other ions making it possible to optimise the chemical mineralisation reaction of the biopolymer membrane.

For example, it could be necessary to adjust the pH of each of the solutions, by adding an acid or a base.

According to a preferred embodiment, the pH of the aqueous solution containing at least one anion is comprised between 7 and 11. This is notably obtained by the addition, into the aqueous solution, of a concentrated ammonia solution (NH$_3$).

According to another preferred embodiment, calcium hydroxide is added to the calcium chloride solution in order to maintain a constant level of calcium ions, this making it possible to avoid a too great acidification of the calcium chloride solution.

As a function of the aqueous solutions used, for example for solutions containing zinc or silver or magnesium or aluminium ions, those skilled in the art will adapt as a function of the needs the other compounds to add to said solutions to maintain a specific pH and/or to optimise the reaction.

Advantageously, in order that the reaction is the most efficient possible, each of the solutions used will be protected from any contamination by the other aqueous solution.

According to an implementation of the method of the invention, the solutions are poured into each of the compartments (1) and (2) after installation of the assembly (3), in such a way as to avoid any contamination.

Device: Vessel and Electrodes

Figure 1:
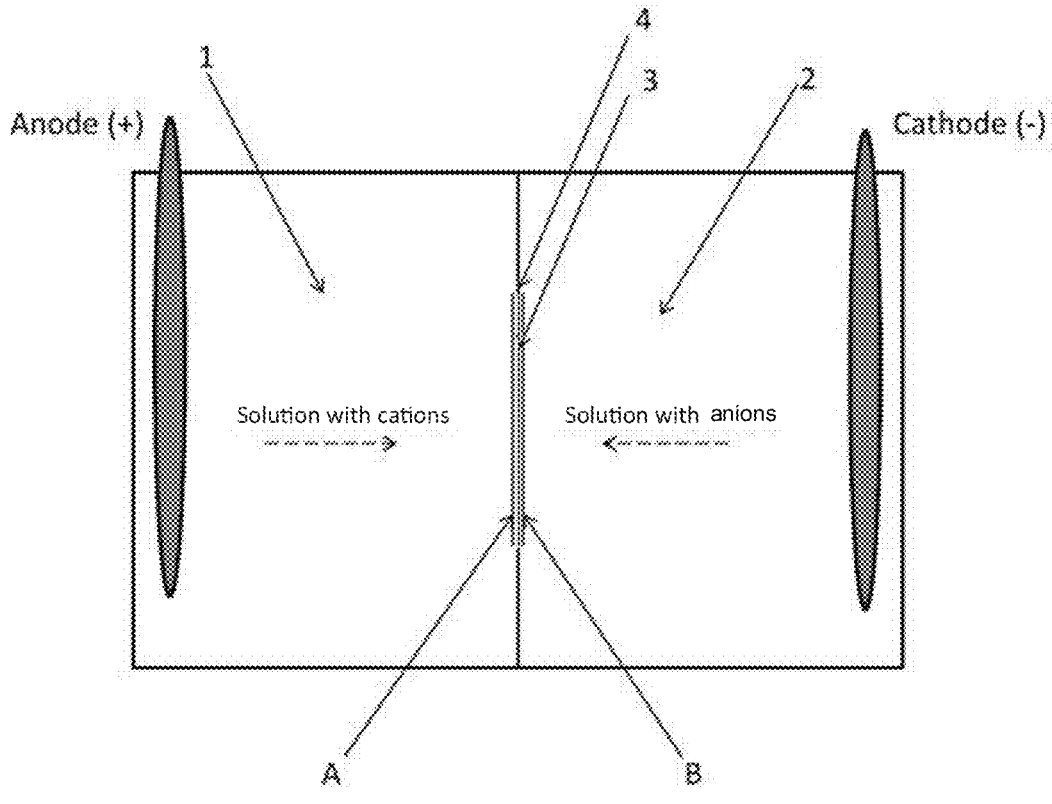
FIG. 1.
Figure 2:
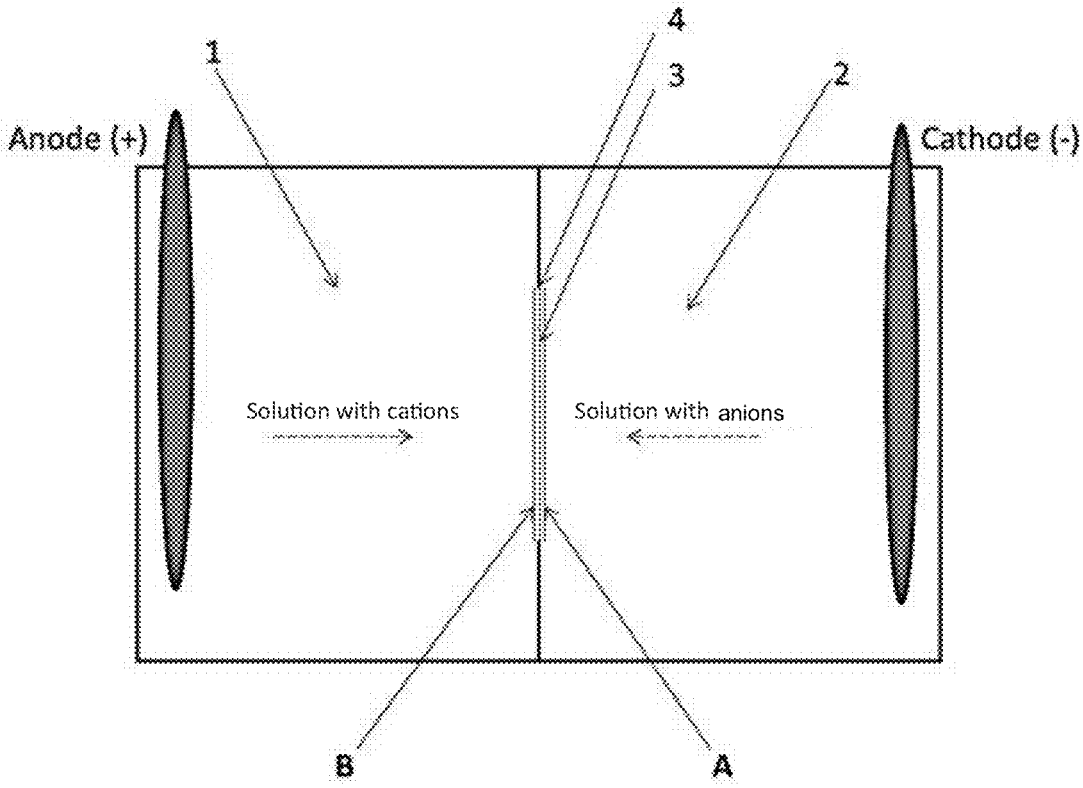
FIG. 2.

A device suited for the implementation of the method according to the invention is represented schematically in FIGS. 1 and 2. It is designated by the name "electrophoresis tank" and includes the vessel and the electrodes.

This device comprises a first compartment (1) and a second compartment (2), each comprising an electrode, the anode being placed in the first compartment (1) and the cathode in the second compartment (2) for the implementation of step (c) of the method.

The anode is defined as being the attraction pole for negative ions (anions) subjected to an electrical field in an electrolysis process. It may for example be constituted of carbon or graphite fibres. The connection elements may advantageously be made of gold or platinum.

The cathode is defined as being the attraction pole for positive ions (cations) subjected to an electrical field in an electrolysis process. It may for example be made of steel.

The device may be constituted of any type of solid inert material, such as glass, plastic or plexiglass.

Advantageously, each compartment has an independent emptying system, which facilitates the carrying out of step (d) of exchange of the solutions and electrodes between the two compartments.

The device also comprises an opening of each of the walls of the first compartment (1) and the second compartment (2) which are brought into contact with one another, which enables the placing in communication of the first and the second compartments.

These openings, also designated "windows", will have a size suited to that of the biopolymer membrane (4). They could for example have a surface area of 10 cm×10 cm, or 15 cm× 15 cm.

According to a preferred embodiment of the invention, the device is equipped with a stirrer, notably immersed in the solution of compartment (1) containing at least one cation, in order to homogenise permanently said solution.

Steps (c) and (c'): Application of an Electrical Voltage Between the Electrodes

During these two steps, an electrical voltage (direct current) is applied between the two electrodes by means of an electrical generator.

Preferably, the intensity is adjusted in such a way as to obtain an actual voltage of 2 to 13 Volts, or 3 to 13 Volts, or better 5 to 12 Volts, or 7 to 10 Volts.

The actual voltage is identical during the two steps (c) and (c'). It is also applied for an equal duration during the two steps, this making it possible to obtain the same level of mineralisation on each face of the biopolymer membrane.

It is to be noted that the voltage varies during the step: for a programmed current intensity, the voltage is going to drop spontaneously when the conductivity is correct.

In addition, the intensity drops at the end of the process because the nanocrystals formed slow down the passage of electrical current.

This electrical voltage is applied, during steps (c) and (c'), for a duration of 8 to 16 hours, preferentially for around 12 hours.

Under the effect of this electrical voltage, the ions are going to be displaced in the solutions surrounding the assembly, and after having traversed the cellulose sheets (A) and (B), are deposited on the biopolymer membrane while forming nanocrystals, rather than the side of the solution containing the cations.

Preferably, during steps (c) and (c'), the aqueous solution containing at least one cation is stirred continuously, to maintain a basic pH and to avoid the dissolution of crystals formed by the genesis of H$^+$ ions.

Preferably, during steps (c) and (c'), the aqueous solution containing at least one cation is saturated with cations by continuous addition of hydroxide of said cation, this making it possible to maintain the pH of the solution containing calcium ions at a value close to 11; in addition, this makes it possible to reconstitute cations constantly. The advantages of this embodiment are described in the patent RU2174848.

Step (d): Turning Over the Biopolymer Membrane

Step (d) making it possible to mineralise the other face of the membrane may be carried out according to two different modalities:

1) either the assembly (3) constituted of the biopolymer membrane and cellulose sheets is removed from the opening between the two compartments, and is turned over in such a way that sheet (A) is henceforth in contact with the aqueous solution of the second compartment, and sheet (B) in contact with the aqueous solution of the first compartment; naturally, all precautions are taken to avoid contamination of each solution with ions coming from the other solution.

2) or an exchange of the solutions and the electrodes of the first and the second compartments is carried out. Thus the cathode is placed in the first compartment (1), in a solution containing at least one anion, and the anode in the second compartment (2), in a solution containing at least one cation, for the carrying out of step (c') such as described above.

According to a first embodiment of the method according to the invention, step (d) is the following: turning over the assembly (3) in such a way that cellulose sheet (A) is on the side of the second compartment and cellulose sheet (B) on the side of the first compartment.

According to a second embodiment of the method according to the invention, step (d) is the following: exchange of solutions and electrodes of the first and the second compartments.

Final Steps (e) and (f) of the Method

At the end of step (c'), the electrical voltage is stopped; and the assembly (3) is removed then rinsed with water. The cellulose sheets (A) and (B) are removed and discarded.

The biopolymer membrane mineralised on its two faces is dried, by any technique known to those skilled in the art.

Advantageously, step (f) of drying the mineralised biopolymer membrane is carried out at a temperature below 35° C.

Preferably, the drying step lasts from 12 to 24 hours.

Mineralised Biopolymer Membrane

One of the subject matters of the present invention is a biopolymer membrane mineralised on its two faces, susceptible to be obtained by the method such as described in the present application.

Another subject matter of the invention is a biopolymer membrane, mineralised on its two faces, obtained by the method described in the present application.

This biopolymer membrane is characterised in that it comprises, on its two faces, nanocrystals organised in the form of platelets and spherical nanoporous crystals having an alveolar structure.

These nanocrystals could notably be constituted of the following mineral compounds:

crystals of a size of the order of a nanometre (of the order of 43 to 45 nm). These nanocrystals next form agglomerates, of micrometric size.

According to a particular embodiment, this membrane is covered on its two faces with calcium phosphate nanocrystals, also designated nanocrystals of calcium phosphate compounds.

According to one aspect of the invention, the mineralised biopolymer membrane is covered, on its two faces, with nanocrystals of apatite of generic formula $Me_{10}(XO_4)_6Y_2$, where Me represents a divalent cation, $XO_4$ a trivalent anionic group and Y a monovalent anion.

The apatitic structure accepts a large number of substituents. Thus, the bivalent cations ($Me^{2+}$) may not only be replaced by bivalent cations ($Mg^{2+}$, $Ag^{2+}$, $Zn^{2+}$, $Sr^{2+}$, $Ba^{2+}$, $Pb^{2+}$), but also by monovalent (e.g. Na+, K+) or trivalent ($La^{3+}$, $Ga^{3+}$, $Eu^{3+}$) cations. Similarly, the trivalent anions $XO_4^{3-}$ may be replaced by bivalent ($CO_3^{2-}$, $SO4^{2-}$, $HPO_4^{2-}$), trivalent ($AsO_4^{3-}$, $VO_4^{3-}$) or tetravalent ($SiO_4^{4-}$) groups. Finally, the Y— groups may also be substituted by monovalent (F—, Cl—) or bivalent ($CO_3^{2-}$, $O^{2-}$, $S^{2-}$) ions.

All possible combinations of cations and anions may be envisaged according to the method of the invention, as a function of the solutions used during the implementation of said method.

Table 2 below, extracted from the thesis of Antoine BOYER entitled "Synthèse, Caractérisation et Evaluation Biologique d'Apatites Phosphocalciques Carbo-Silicatées" (Synthesis, characterisation and biological evaluation of carbo-silicate calcium phosphate apatites), presents different types of apatite being able to be obtained by the method according to the invention, and having a biological interest.

TABLE 2

| | | Different types of apatite | |
|---|---|---|---|
| | Substitutions | Theorical chemical formula | Notations |
| Site $Ca^{2+}$ | $Ag^+$ | $Ca_{10-x}Ag_x(PO_4)_6(OH)_{2-x}$ | Ag-HA |
| | $Mg^{2+}$ | $Ca_{10-x}Mg_x(PO_4)_6(OH)_2$ | Mg-HA |
| | $Sr^{2+}$ | $Ca_{10-x}Sr_x(PO_4)_6(OH)_2$ | Sr-HA |
| | $Zn^{2+}$ | $Ca_{10-x}Zn_x(PO_4)_6(OH)_2$ | Zn-HA |
| Site B ($PO_4^{3-}$) | $CO_3^{2-}$ | $Ca_{10-x}(PO_4)_{6-x}(CO_3)_x(OH)_{2-x}$ | $C_B$-HA |
| | $HPO_4^{2-}$ | $Ca_{10-x}(PO_4)_{6-x}(HPO_4)_x(OH)_{2-x}$ | |
| | $SiO_4^{4-}$ | $Ca_{10}(PO_4)_{6-x}(SiO_4)_x(OH)_{2-x}$ | Si-HA |
| Site A (OH⁻) | $Cl^-$ | $Ca_{10}(PO_4)_6(OH)_{2-2x}Cl_{2x}$ | Cl-HA |
| | $CO_3^{2-}$ | $Ca_{10}(PO_4)_6(OH)_{2-2x}(CO_3)$ | $C_A$-HA |
| | $F^-$ | $Ca_{10}(PO_4)_6(OH)_{2-2x}F_{2x}$ | F-HA |
| Mixed Sites A/B | $CO_3^{2-}$ | $Ca_{10-x+u}(PO_4)_{6-x}(CO_3)_x(OH)_{2-x+2u-2y}(CO_3)_y$ | CA/B-HA |

Calcium phosphate compounds, notably selected from the following:

Hydroxyapatite; and/or

Deficient hydroxyapatite doped with fluoride, silver, or zinc ions; and/or

A poly-substituted apatite or a deficient hydroxy-, fluoro- or carboxy-apatite; and/or Brushite (dicalcium phosphate dihydrate: $CaHPO_4·2H_2O$); and/or Calcium phosphate compounds with labile hydrogen-phosphate groups, Magnesium sulphate, or Aluminium sulphate, or Any combination of these mineral compounds The precipitation of ions on the biopolymer membrane generates the formation of nanocrystals, defined as being From a biological viewpoint, magnesium is interesting in that it plays a role in bone remodelling at the moment of calcification. Silver has antibacterial properties. Strontium has been found in the calcified tissues of bone and seems to be an important actor in its mineralisation. Zinc has an inhibitor effect on in vitro osteoclastic activity.

As regards anionic substitutions, the presence of fluoride ions F— is determining in bone growth. The absence of F— limits bone densification, and conversely, its too high concentration generates osteosclerosis. Cl— ions have the capacity to develop an acid environment on the surface of the bone, which activates the osteoclasts in the resorption process in order to solubilise the alkaline salts of the bone mineral.

Thus, the incorporation of such or such an ion in the apatitic structure is capable of changing and potentially improving the bioactivity of the mineralised biopolymer membrane.

According to a particular aspect of the invention, the mineralised biopolymer membrane is covered, on its two faces, with nanocrystals of hydroxyapatite of formula $Ca_5$ $(PO_4)_3(OH)$, often written $Ca_{10}(PO_4)_6(OH)_2$ to underline the fact that the lattice of the crystalline structure comprises two molecules.

This so-called "stoichiometric" hydroxyapatite contains 39% Ca, 18.5% P and 3.38% OH, the percentages being expressed in weight/total weight of the mineral. Hydroxyapatite is the main mineral component of dental enamel, dentine and bone. The CAS number of hydroxyapatite is 12167-74-7.

According to another particular aspect of the invention, the mineralised biopolymer membrane is covered, on its two faces, with nanocrystals of brushite (dicalcium phosphate dihydrate, formula $CaHPO_4·2H_2O$) and nanocrystals of calcium deficient carbonated hydroxyapatite.

The mineralised membrane according to the invention has numerous advantages and notably a capacity of very rapid resorption for a hydroxyapatite, after its introduction in a living organism.

The mineralised membranes according to the invention may advantageously be totally resorbed in a time comprised between 5 and 60 days after their implantation in a living organism. A membrane according to the invention could in particular be resorbed in less than 10 days, in less than 15 days, in less than 20 days, in less than 25 days, in less than 30 days, in less than 40 days, in less than 50 days or in less than 60 days after its implantation in a living organism, human or animal.

These resorption times have been measured in several animal models (rabbits, rats, dogs) as is presented in example 6. It will be noted that in most cases, the membrane or the powder is resorbed in less than 25 days; however, for certain particular therapeutic applications, such as for example the regeneration of nerves, it is necessary to wait up to 60 days to observe total resorption.

The membrane according to the invention is perfectly biocompatible, without tumorigenic effect, without toxicity, without immunogenic effect, which avoids the rejection or the encapsulation of the membrane, thanks to a high capacity for bio-integration in the receiving organism.

The present invention also relates to a biopolymer membrane mineralised on its two faces with nanocrystals of mineral compounds organised in the form of platelets and spherical nanoporous crystals having an alveolar structure.

These mineral compounds could be one of those cited previously, notably chosen from:

Calcium phosphate compounds, notably chosen from the following:

Hydroxyapatite; and/or

Deficient hydroxyapatite doped with fluoride, silver, or zinc ions; and/or

A poly-substituted apatite or a deficient hydroxy-, fluoro- or carboxy-apatite; and/or Brushite (dicalcium phosphate dihydrate: $CaHPO_4·2H_2O$); and/or Calcium phosphate compounds with labile hydrogen-phosphate groups, Magnesium sulphate, or Aluminium sulphate, or Any combination of these mineral compounds.

The present invention relates in particular to a biopolymer membrane mineralised on its two faces with calcium phosphate nanocrystals organised in the form of platelets and spherical nanoporous crystals having an alveolar structure.

Example 7 of the present application shows the structural characteristics of this membrane, which has never been observed until now. In particular, the organisation of the nanocrystals in the form of platelets and spherical nanoporous crystals having an alveolar structure is not observed on the control samples, which have coarse agglomerates and non-homogeneous structures.

This structure of nanocrystals deposited on the membrane according to the invention is particularly advantageous for the following reasons:

the platelets do not contain "needle" structures liable to injure the tissues of the organism into which the membrane will be introduced;

the spherical crystals having an alveolar structure make it possible to fix biological proteins circulating around the membrane, after its implantation within a living organism, said proteins actively participating in the healing and in the resorption of the implanted material.

According to a particular embodiment, the biopolymer constituting the membrane is collagen.

The present invention also relates to a biopolymer membrane mineralised on its two faces with nanocrystals of mineral compounds, notably calcium phosphate, organised in the form of platelets and spherical nanoporous crystals having an alveolar structure, susceptible to be obtained according to the method of the invention, or obtained according to the method of the invention.

Other subject matters of the invention are particular pharmaceutical formulations of one of these mineralised biopolymer membranes:

a powder constituted of one of these biopolymer membranes reduced into powder, by a means chosen from those known to those skilled in the art, or instead a solution comprising said powder in suspension in a pharmaceutically acceptable vehicle.

A pharmaceutically acceptable vehicle designates vehicles or excipients, that is to say compounds not having specific action on the organism. These vehicles or excipients are pharmaceutically acceptable, which signifies that they can be administered to a living organism without generation of significant deleterious effects.

Thus, according to the invention, the powder obtained comprises a biopolymer, such as defined previously, and nanocrystals, notably of hydroxyapatite. In particular, the nanocrystals will be organised in the form of platelets and spherical nanoporous crystals having an alveolar structure.

Therapeutic Uses

Said mineralised membranes could be introduced into a living organism, notably a human being, in order to repair bone, cartilage, or other structural organ disorders.

A powder of mineralised membrane, or a solution containing it, could be administered to an individual according to any mode of administration known to those skilled in the art, notably by oral, sublingual, inhalation, subcutaneous, intramuscular, intravenous, transdermic, ocular or rectal route.

Thus, the present invention relates to a biopolymer membrane, or a powder, or a solution such as described above, for the therapeutic use thereof in the treatment of bone, cartilage, pancreatic, renal, urethral, urethral and vesical, testicular, ovarian, intestinal, hepatic, neurological, cardiac, tympanic, ocular, urinary, gynaecological, pulmonary, bronchial, tracheal, vascular, conjunctive, cutaneous, mucosal, dental, gingival and/or haematopoietic tissue and immune disorders.

In particular, the present invention relates to a biopolymer membrane, or a powder, or a solution such as described above, for the therapeutic use thereof in the treatment of pancreatic disorders.

In particular, the present invention relates to a biopolymer membrane, or a powder, or a solution such as described above, for the therapeutic use thereof in the treatment of renal disorders.

In particular, the present invention relates to a biopolymer membrane, or a powder, or a solution such as described above, for the therapeutic use thereof in the treatment of urinary disorders.

In particular, the present invention relates to a biopolymer membrane, or a powder, or a solution such as described above, for the therapeutic use thereof in the treatment of dental disorders.

In particular, the present invention relates to a biopolymer membrane, or a powder, or a solution such as described above, for the therapeutic use thereof in the treatment of gynaecological disorders.

In particular, the present invention relates to a biopolymer membrane, or a powder, or a solution such as described above, for the therapeutic use thereof in the treatment of haematopoietic and immune disorders.

In particular, the present invention relates to a biopolymer membrane, or a powder, or a solution such as described above, for the therapeutic use thereof in the treatment of inflammation.

In particular, the present invention relates to a biopolymer membrane, or a powder, or a solution such as described above, for the therapeutic use thereof in the treatment of disorders linked to a high oxidant capacity.

The invention also pertains to a therapeutic method for the treatment of bone, cartilage, pancreatic, renal, urethral, urethral and vesical, testicular, ovarian, intestinal, hepatic, neurological, cardiac, tympanic, ocular, urinary, gynaecological, pulmonary, bronchial, tracheal, vascular, conjunctive, cutaneous, mucosal, dental, gingival and/or haematopoietic tissue and immune disorders in human beings, comprising the administration to said human being of an effective amount of a mineralised biopolymer membrane, a powder or a solution such as described in the present application.

The invention also relates to a dietary supplement, comprising a powder or a solution such as described above.

The powder or solution according to the invention only acts in the case of inflammation, injury or illness: in addition, its activity is limited over time by the available amounts. This powder or solution does not lead to a phenomenon of anarchic or uncontrolled cell replication. It has no action on cell division without prior traumatism, and thus is not a growth factor.

The mineralised biopolymer membrane may be used in surgery, as class 3 "DMI" material during an intracorporal surgical intervention Alone and dry; or Associated with antibiotics (C3G, Vancomycin, gentamycin, etc.) or pro-regenerative hormones (Ocytocin, Serotonin, etc.).

It may be used in the form of a "plate" for an implantation in contact with organs or a surface deposition. It is not necessary to use a plate of particular shape, the regeneration of the organ organising itself.

Tissue regeneration will start on site as of the resorption of the material in post-surgical physiological conditions with inflammatory mediators and host cells (macrophages M1 and M2, differentiated cells and stem cells).

When the mineralised biopolymer membrane is in the form of injectable powder (reconstituted in physiological serum or xylocaine), it may be used:

in intra-bone (for local or general usage), in intra-articular, in soft tissues (e.g.: in the nasal septum to regenerate a defect of the septum) or in mesotherapy, in eye drops or in intravitreal injection, in auricular or nasal drops, in capillary or cutaneous solution, in a tube of resorbable collagen or chitosan connecting neural ends, or in intravascular (stimulates the neo-angiogenesis behind tissue regeneration phenomena).

The powder may also be administered by spraying:

Bronchial and pulmonary, or

Nasal (for a cerebral route), or

Cutaneous (powder alone or in preparation in a specific cream).

EXAMPLES

Example 1. Method for Mineralising a Collagen Membrane

In this example, a collagen membrane of a size of 100 cm$^2$ (10x10) is mineralised on its two faces with hydroxyapatite nanocrystals, according to the protocol described hereafter.

The vessel used is made of glass. The window (communication opening between the two compartments) is 10×10 cm.

1—Preparation of Solutions

Two solutions of calcium chloride and ammonium phosphate are prepared, by complete dissolution of powders in beakers using dedicated pipettes to obtain 2×2.5 litres of:

Ammonium phosphate (with one, two or three solutions of substituted ammonium phosphate ($NH_4H_2PO_4$, $(NH_4)_2HPO_4$, $(NH_4)_3PO_4$)), and Calcium chloride into which $Ca(OH)_2$ is added later.

2—Preparation of the "Sandwich" (Assembly (3))

Cellulose sheets are placed on each face of the collagen membrane.

3—Filling of the Tanks:

This must be done at the same speed on each side without mixing of liquids, to avoid the pressure of the most filled compartment deforming the assembly.

Several drops of a concentrated solution of $NH_3$ are added to the compartment comprising $PO_4^{3-}$ ions.

A sodium hydroxide solution is added to the compartment containing $Ca^{++}$ ions 4—Arrangement of the Electrodes and Stirrer The negative electrode (cathode) is made of steel, it is immersed in the bath of ammonium phosphate.

The positive electrode (anode) is made of solid graphite (carbon) or graphite (carbon tissue), it is immersed in the bath of $Ca^{++}$ with the stirrer.

5—Starting the Method

A direct current is applied to the electrodes in such a way as to obtain an actual voltage comprised between 2 Volts and 13 Volts.

The method takes place at room temperature for 24 hours in total, during which the electrodes and the solutions are inverted after 12 hours.

6—End of Procedure

Gently, the stirrer and the electrophoresis are stopped. The electrodes are removed without contaminating the solutions.

The collagen membrane imbibed with hydroxyapatite nanocrystals is removed and dried at a temperature not exceeding 30-35° C. (almost at room temperature) for around 12 to 24 hours.

Example 2. Observed Effects of the Administration of the Products According to the Invention Positive effects of the administration of these products according to the invention have been observed in the following tissues:

Bone (treatment of losses of substance and pseudarthrosis, treatment of osteomyelitis)

Cartilage (hyaline and articular) (cartilage regeneration)

Renal (haemostasis and section reinforcement of renal polar resection)

Hepatic (filling of liver cysts, haemostasis and hepatic regeneration guide after hepatectomy)

Neurological (diastasis regeneration on peripheral nerves)

Cardiac (revascularisation and myocardial regeneration after heart attack)

Tympanic, ocular (tympan regeneration, treatment of congenital glaucoma)

Urinary (e.g.: hypospadias healing guide)

Gynaecological (intravascular treatment of female sterility, regeneration of the cervix)

Pulmonary (filling of cysts or loss of substance, reinforcement of bronchial suture)

Conjunctive and support tissue (stress incontinence)

Cutaneous and mucosal (wound, ulcer, gingivopathy, etc.), and

Dental (treatment of tooth decay, grafting and creation of teeth, bone preparation before implantology act).

Example 3. Particular Use in Intra-Medullar Bone Injection: Remote Action

The "powder" form may be reconstituted in the form of an injectable solution (1 ml of dry powder diluted in 2 to 4 ml of physiological serum and/or 1% xylocaine for example). It may next be injected into the bone marrow using a syringe and a bone trocar, for example at the level of the iliac crest.

The effect generated at the level of hematopoietic and immune tissue is going to lead to a decrease in inflammatory reactions.

For example, an improvement and decrease in inflammation on the section of a hepatectomy may be observed after post-operative injection into the iliac crest.

The administration of the powder in suspension has a positive action at the level of a damaged zone of the myocardium, following a post-crisis injection into the iliac crest.

Example 4. Oral and Buccal Mucosal Usage as Dietary Supplement

The plates and the powder may be administered orally. Absorption takes place through the jugal and gingival mucous.

The administration is twice a day for 30 days. The observed effect is:

local, with an improvement in the trophicity of gingival tissue, recovered tension of the dental ligament if the teeth move; and general, with a decrease in joint paint and arthrosis as of the 5th day of taking, an improvement in mood and general condition.

In individuals with type 2 diabetes, positive effects were observed on glycaemic control after twice daily administration of the powder according to the invention.

Figure 3:
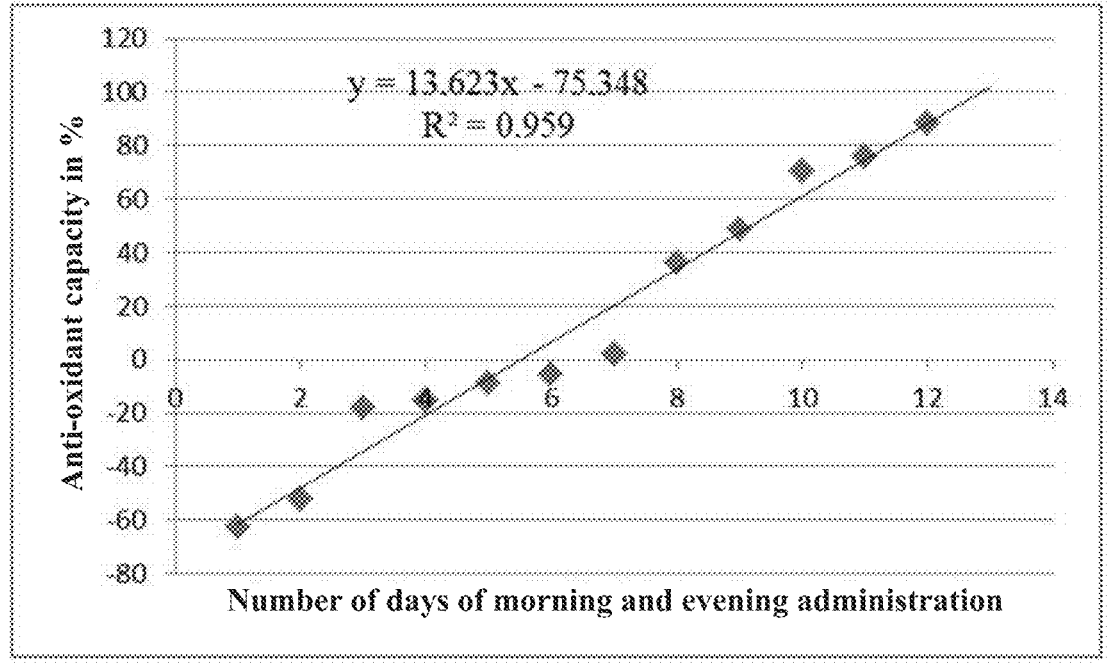
FIG. 3.

Example 5. Anti-Oxidant Action of the Product after Oral Administration, Measured in Urine The ingestion by individuals, morning and evening, of a powder according to the present invention causes a steady increase in the total antioxidant capacity measured on samples of urine, as shown in FIG. 3.

TAC (total antioxidant capacity) is a biomarker that measures the antioxidant potential of body fluids. Those skilled in the art know the different test methods used to measure TAC, and a good correlation has been found between the results obtained by different techniques. The samples of urine are obtained in a non-invasive manner, which has a considerable interest for the study of the antioxidant status of the body.

The investigation protocol is summarised below:

3 participants in good general health were enrolled in the study, two maLes aged 67 and 75 years old and a 25 year old female. FIG. 3 presents the results obtained in the 67 year old male; similar results were observed in the two other individuals tested.

Control samples of morning urine were taken at 7 hours on an empty stomach, then at 8 hours and at 19 hours, according to the normal protocol.

The determination of the total antioxidant capacity of the samples was carried out by a conventional coulometric analysis method, measuring the amount of electricity consumed or produced during an electrolysis.

The results are presented in percentages compared to the control samples, the "standard" used being rutin, a flavonoid having recognised antioxidant properties. The urine samples were assayed with total antioxidant capacities, the equivalence values of which are 285 to 1647 mg of rutin (Ru) for 1 dm$^3$ (litre).

FIG. 3 shows the clear increase in the total antioxidant capacity of the urine sampled in a patient consuming twice daily a powder according to the invention, between the first days (up to the 6$^{th}$ day, the capacity measured is "oxidant" and not anti-oxidant), and days 10-12 where the percentage antioxidant capacity of the urine samples is high.

Example 6. Resorption of the Membrane Obtained by the Method According to the Invention, in Different Animal Models (Rat, Rabbit, Dog)

The resorption of the membrane is determined by histological analysis after implantation in the animal (rat, rabbit or dog) in a particular tissue, then after biopsy of the implanted zone at different times.

The observed resorption is rapid, the progressive disappearance of the implanted material takes place progressively in small blood vessels (neo-angiogenesis), conjunctive tissue then cellularised functional tissue.

The specific study of the resorption times of the mineralised membrane, in the form of plate or powder, carried out in the subcutaneous tissue of dogs and rabbits, has shown that:

At D2-D3 post-implantation (pi): partial resorption of the mineralised membrane, with presence of a large proportion of eosinophilic granulocytes. The collagen fibres are swollen.

At D5-D7 pi: important resorption of the mineralised membrane, with presence of giant multinucleated cells, lymphocytes and macrophages.

At D14 pi: a high proportion of mononuclear cells within several islands of remaining mineralised membrane. Instead of resorbed composite, there is young and mature granulation tissue with vessels formed by typical flattened endotheliocytes filled with blood cells. The transformation of the granulations into fibrous tissue is also noted.

At D25 pi: instead of the membrane which has disappeared, isolated islands of mature conjunctive tissue in full development are found, surrounded by macrophages, giant cells, and lymphocytes. The membrane has not caused a rejection reaction. The morphological changes in the implantation zone of the membrane correspond to a strong proliferative cellular reaction with replacement of collagen-apatite complex by fibrous conjunctive tissue.

Tables 3 to 8 below show the histological evolution observed as a function of the host tissue and the time after implantation (pi: post implantation).

TABLE 3

Implantation of a mineralised membrane for reconstruction of a bone (dog, n = 16)

| $3^{rd}$ day pi | $14^{th}$ day pi | $25^{th}$ day pi |
|---|---|---|
| The implanted material is partially resorbed but is still present in majority. It is constituted of conjunctive tissue, loose on the periphery. | The material is resorbed massively It is surrounded by macrophages and numerous giant cells with foreign bodies. | Implanted material is not found. The tissue formed has blood vessels, osteoclasts, osteoblasts and osteocytes. |

TABLE 4

Implantation of a mineralised membrane in the lung and the pleura (rabbit, n = 8)

| $3^{rd}$ day pi | $7^{th}$ day pi | $14^{th}$ day pi | $25^{th}$ day pi |
|---|---|---|---|
| Rapid and partial biodegradation of the material, presence of eosinophilic polynuclear cells in thinned and lysated collagen fibres | Complete resorption of the implanted material, formation of "pre-capillaries" instead (beginnings of blood capillaries) formed by reticulocytes and mesenchymal cells | Beginnings of blood capillaries with A vasoactive wall, Poorly differentiated cells with formation of the erythrocyte rosette inside Mesenchymal cells entering into mitosis around the walls Pulmonary parenchyma surrounding the conjunction tissue formed Accumulation of numerous neutrophilic and eosinophilic polynuclear cells | Blood capillaries containing circulating blood cells, surrounded by conjunctive tissue and pulmonary parenchyma |

TABLE 5

Liver - implantation of a mineralised membrane in a created cystic cavity (rats, n = 33)

| $7^{th}$ day pi | $14^{th}$ day pi | $25^{th}$ day pi |
|---|---|---|
| Appearance of granulation tissue, decrease of exudates | Continuation of the process of formation of granulation tissue instead of the composite | Maturation of this granulation tissue with presence of conjunctive tissue with organotypical structures: hepatocytes and cholangioles with signs of regional rechannelling of the biliary tracts. The sinusoidal and biliary capillaries have conserved their lumen and showed no sign of disruption of blood microcirculation nor the excretion of bile. Hypertrophy of adjacent hepatocytes with increase in their mitotic activity (multiplied threefold) and increase in the synthesis of Ki-67 protein (also multiplied threefold). |

TABLE 6

Injection in bone marrow (iliac crest) of a powder constituted of ground mineralised membrane, and hepatectomy (dog, n = 5)

| $14^{th}$ day pi | $25^{th}$ day pi | $45^{th}$ day pi |
|---|---|---|
| Complete disappearance of the implanted material. Between the bone trabeculae, numerous pluripotent mesenchymal stem cells are found | Numerous pluripotent mesenchymal stem cells in the bone marrow but also in the general circulation and at the level of the hepatectomy section (numerous stem cells in mitosis) | Within the hepatectomy section, phenomenon of hepatic regeneration with appearance of newly formed interlobar bile ducts |

TABLE 7

| Injection in the bone marrow (iliac crest) of a powder constituted of ground mineralised membrane, and link with cerebral degenerative disease through loss of microvascularisation, loss of neurones and proliferation of glial cells. (dog, n = 1) | | |
|---|---|---|
| 7th day pi | 14th day pi | 45th day pi |
| In the marrow: resorption of the material, presence of pluripotent mesenchymal stem cells and collagen fibres (extracellular structure). | At the cerebral level: A biopsy of the cerebral cortex (gyrus) highlights minor modifications of the neurocytes in the midst of a lack of glial cells | At the level of the bone marrow: capillaries in the course of growth with red blood cells in the lumen, Cluster of pluripotent mesenchymal stem cells. In the cerebral cortex: Activation of angiogenesis (Newly formed capillary. Endotheliocyte mitoses). Reduction in the number of glial cells and restoration of neurocytes |

TABLE 8

| Treatment of the cutting of a rat peripheral nerve (rat, n = 5). A loss of nervous substance of 1 cm was observed on the sciatic nerve. A solution composed of powder derived from grinding of a mineralised membrane was placed in a tube of keratin which joins the 2 ends of the broken nerve. The clinical observations are recorded in table 8 below. | | | |
|---|---|---|---|
| 14th day pi | 25th day pi | 60th day pi | 90th day pi |
| Separate biodegradation of the implant and formation of neuronal cell regeneration. Formation of a microvascular bed. | Myelin fibres in formation in the form of axial cylinders. This process is organised by neurolemmocytes | The injected powder is completely biodegraded and, instead of diastasis, a fragment of the sciatic nerve is formed, composed of amyelinic fibres ($\approx$71% of their number in the intact sciatic nerve) and myelin ($\approx$68% of their number in the intact sciatic nerve). The nerve bundles are surrounded by conjunctive tissue. | Presence of: Micro-vessels in the restored fragment of the operated sciatic nerve: with arterioles, venules (containing erythrocytes and endotelocytes) Conjunctive tissue Myelinated nerve fibres |

Example 7. Molecular Characterisation of the Calcium Phosphate Crystals Present on the Membranes Obtained by the Method According to the Invention The calcium phosphate nanocrystals obtained by several different mineralisation methods were compared:

Sample 7: Collagen membrane mineralised for 24 hours, without Cellophane —Without Electrophoresis Sample 4: Collagen membrane mineralised for 24 hours, With Cellophane—Without Electrophoresis Sample 6: Collagen membrane mineralised for 24 hours, Without Cellophane—With Electrophoresis Sample 5: Collagen membrane mineralised for 24 hours, With Cellophane—With Electrophoresis, i.e. according to the method of the invention.

The samples were analysed with the following characterisation techniques:

Zeiss Supra 55VP scanning electron microscope (SEM). Observations made without conductive surface deposition and at low voltage to as not to mask the morphology of the agglomerates and calcium phosphate crystals formed on the surface of the collagen fibres.

Bruker D8 Advance 9/9 XRD X-ray diffractometer (XRD) equipped with a Lynx-Eye Position Sensitive detector (angle opening 2.9460), using CuK a radiation (40 kV and 40 mA). The diffractograms were analysed using TOPAS-64 V6 software.

VERTEX 70 infrared (IR) spectrometer (Bruker Optics, France), equipped with an attenuated total reflectance system (Quest ATR diamond; Specac, USA). In order to be able to compare the spectra with each other a "curve fitting" procedure with addition of a control was carried out, according to the procedure developed in the thesis of Baptiste Charbonnier (EMSE, 09/12/2016).

A—Analysis by Electron Microscopy

Figure 4:
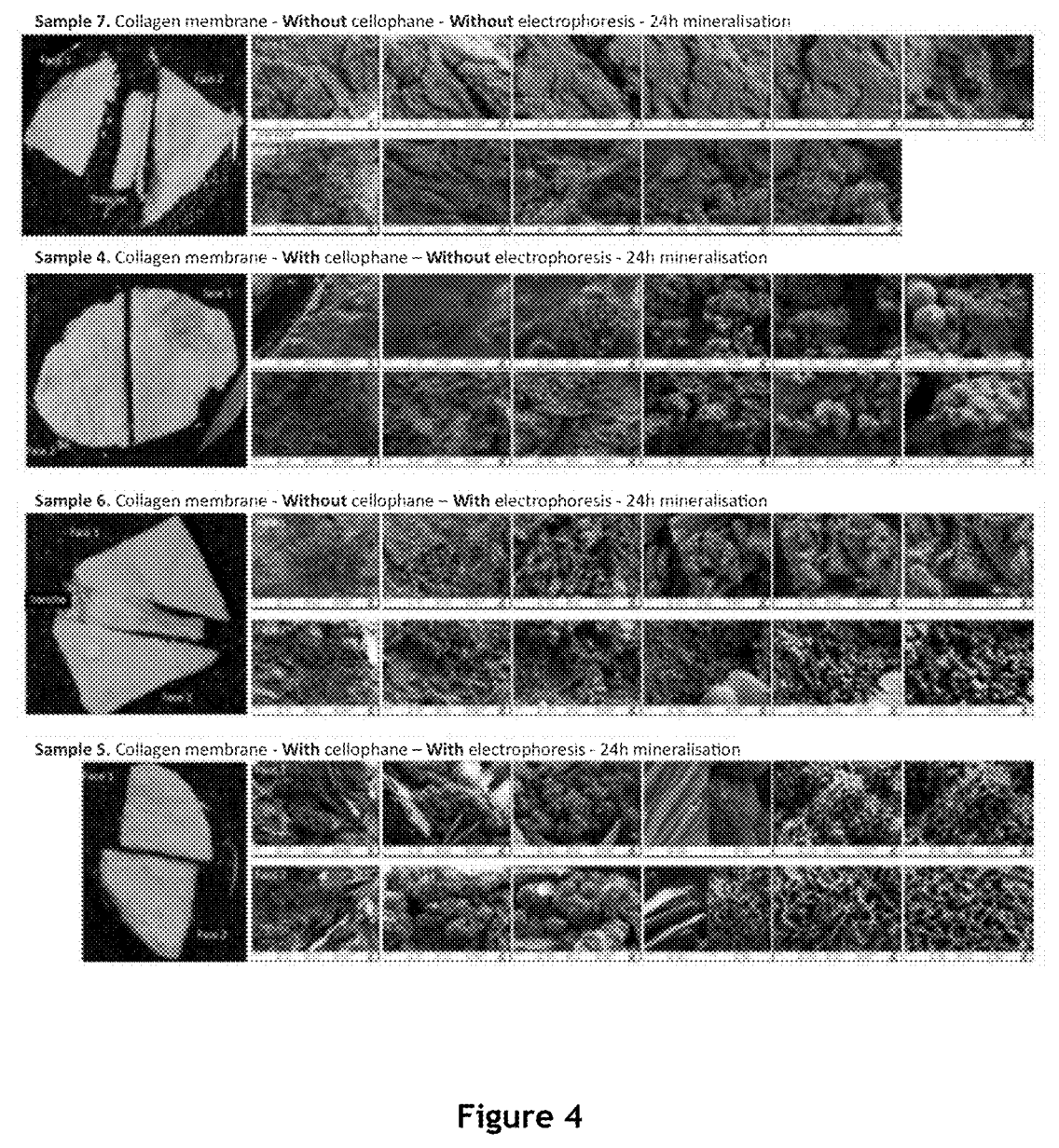

FIGS. 4 and 5 show images obtained by scanning electron microscopy (SEM) on the two faces of the mineralised collagen membranes, at several enlargements.

The images show that:

sample 7 obtained without a porous cellophane membrane and without electrophoresis is very thick, highly mineralised and quite dense, even obstructed/sealed off for Face 1 (enlargement×10.000). Macroscopically, the mineralised matrix 7 resembles a strip of plaster. The morphology of the surface agglomerates is coarse on both sides of the membrane at low enlargement. A relative inhomogeneity of the morphology of the CaP crystals appears at greater enlargement (×10.000) between the 2 faces of the membrane.

sample 4 obtained with a porous membrane of cellophane and without electrophoresis is unlike sample 7 very thin and very little mineralised. Face 1 clearly shows the collagen matrix (yellow colour in the photo). The mineral layer on this surface is very thin but very dense; the porosity seems totally closed/obstructed. Small balls of mineral ≤1 μm in diameter are randomly visible on this Face (1) whereas they are not on the other Face (2). The difference between Face 1 and Face 2 is obvious.

sample 6 obtained without porous cellophane membrane and with electrophoresis is like sample 7 relatively thick, with however clear thickness variations (up to 100%, photo Sample 6). The mineral formed on either side of the collagen membrane (i.e., Faces 1 and 2) is relatively more porous than for sample 7 with on one side (Face 1) coarse, randomly dispersed agglomerates (around 10 μm diameter) and an inhomogeneous nano-structure, and on the other side (Face 2) a surface composed of small balls of mineral ≤1 μm in diameter. The concentration of these balls is clearly higher than for Face 1 of sample 4.

sample 5 obtained with a porous cellophane membrane and with electrophoresis is significantly different from the 3 others whether it is at the membrane scale, the agglomerate scale or the nanometric scale.

Macroscopically, the membrane has the same aspect on both faces (photo, Sample 5). The thickness and the colour of mineral is relatively homogeneous on both with small shiny crystals.

These crystals, visible on the SEM images, are platelets/sheets of calcium phosphate quite characteristic of the Brushite phase (CaHPO4, 2H2O), i.e. "leaflet shaped". These platelets are relatively large, up to more than 100 μm long, and thin, <1 μm thickness (growth along a quite precise crystallographic plane). The surfaces are relatively porous with rugged topographies.

This topography is the result of the association of crystals in the form of platelets and spherical nanoporous crystals. The latter have a diameter of ten or so μm and have submicropores resembling the cells of a hive. The walls of these cells, i.e., the crystal, are very, very thin, of the order of a nanometre.

FIG. 5 shows the images obtained by scanning electron microscopy on the two faces of the membrane, at ×20,000 and ×30,000 enlargements.

This morphology of the nanocrystals is very particular and very interesting. Indeed, the size and the shape of the porosity can trap biological proteins of interest (growth or healing factors, such as BMP2, etc). The thin walls with the shape of the cells of a hive (alveola) considerably increase the exchange surface with fluids and thus the interaction capacity of these nanocrystals with said fluids.

In conclusion, the method for mineralising collagen membrane according to the invention, associating a porous membrane (cellophane type) and an electrical field, effectively form unique and oriented crystal morphologies, as well as a homogeneous distribution of these crystals on either side of the membrane.

B— Diffractograms of the Manually Ground Mineralised Membranes

FIG. 6 represents a comparison of the diffraction spectra obtained on the ground membranes of samples 7, 4, 6 and 5.

All the samples have spectra with rather broad and not very intense diffraction peaks.

Samples 7 and 4, obtained without electrophoresis, have a single and unique detectable crystalline phase, the crystallographic structure of which is close to that of hydroxy-apatite (indexed with the PDF file 09-0432).

Samples 6 and 5, obtained with electrophoresis, have two crystalline phases, the crystallographic structure of which is for one close to that of hydroxyapatite (HA, PDF 09-0432) and for the other clearly that of Brushite (PDF 09-0077). The diffraction peaks relative to Brushite are also narrower than those of the apatitic structure indicating that the local order of Brushite crystals is higher than that of apatite crystals.

These results, associated with the preceding results, confirm that the platelets observed by SEM on sample 5 (method according to the invention) are rather well crystallised Brushite crystals with growth along a quite precise crystallographic plane, and that the submicroporous balls are crystals of crystallographic structure close to that of hydroxyapatite (HA).

C— Infrared (IR) Spectra Obtained on the Normalised, Manually Ground Mineralised Membranes The results confirm that sample 4, elaborated with a porous cellophane membrane and without electrophoresis, is less mineralised than the other samples.

Samples 7 and 6 obtained without cellophane membrane have equivalent IR spectra with bands characteristic of phosphate groups (1200-900 cm$^{-1}$, 620-480 cm$^{-1}$), hydroxide groups (3500 cm$^{-1}$, 620 cm$^{-1}$) and carbonate groups (1700-1200 cm$^{-1}$, 910-830 cm$^{-1}$). These samples are thus composed essentially of deficient carbonated hydroxyapatites of generic formula:

$$Ca10-x(PO4)6-x \cdot (HPO4^{2-} \text{ or } CO3^{2-})x \cdot (OH \text{ or } 1/2CO3)2-x \text{ with } 0 \leq x \leq 2$$

These samples also exhibit a band at 542 cm$^{-1}$ relative to labile HPO4 groups (Cf. FIG. 7, lower graph). This band is attributable either to HPO4 ions trapped outside of the apatite structure or in Brushite.

In an equivalent manner, sample 5, elaborated with a porous cellophane membrane and under electrophoresis, has bands relative to apatite groups and a band relative to labile HPO4 groups (Cf. FIG. 7, upper graph). However, the bands relative to apatite are less intense than those observed on the spectrum of sample 7, whereas the band at 542 cm$^{-1}$, relative to labile HPO4 groups, is more intense. These semi-quantitative results confirm the preceding SEM and DRX observations.

Further, sample 7 seems to be more mineralised than sample 5 (FIG. 7, phosphate band at 560 cm$^{-1}$/collagen band at 510 cm$^{-1}$). This result also confirms the visual observations made with SEM and the dense and obstructed/sealed off appearance of the surfaces of the samples obtained without electrophoresis.

In conclusion, the method according to the invention implementing a controlled mineralisation of porous organic membrane by means of a porous cellophane membrane and an electrical field effectively makes it possible to obtain a relatively homogeneous mineral density within the organic membrane, as well as a unique morphology of CaP crystals and composition of the mineral. The morphological characteristics of the crystals of calcium deficient carbonated hydroxyapatite, highly oriented and shaped like the cell of a hive, are particularly interesting for biological applications (e.g., trapping proteins within the submicroporosity, very high exchange surface/weight of crystal ratio).

BIBLIOGRAPHIC REFERENCES

EP 3181158
WO 2008/096334
RU2410040
WO 2013/111077
WO 2013/190534
U.S. Pat. No. 6,395,036

23

WO 2008/096334
EP 3021883
RU2174848
U.S. Pat. No. 5,532,217
U.S. Pat. No. 5,739,286
U.S. Pat. No. 6,589,590
Thesis of Antoine BOYER entitled "SYNTHESE, CAR-ACTERISATION ET EVALUATION BIOLOGIQUE D'APATITES PHOSPHOCALCIQUES CARBO-SILICA-TEES", defended at Saint-Etienne on the 17ᵗʰ April 2014.

The invention claimed is:

1. A biopolymer membrane mineralised on its two faces with nanocrystals of mineral compounds organised in the form of platelets and spherical nanoporous crystals having an alveolar structure, wherein said nanocrystals are constituted of:

a) hydroxyapatite and/or deficient hydroxyapatite doped with fluoride, silver, or zinc ions and/or poly-substituted apatite or deficient hydroxy-, fluoro- or carboxy-apatite, b) brushite, and c) calcium phosphate compounds with labile hydrogen-phosphate groups; and wherein said mineralised biopolymer membrane resorbs in 5 to 60 days after implantation in a living organism.

2. The biopolymer membrane according to claim 1, wherein the biopolymer is collagen.

3. A biopolymer membrane mineralised on its two faces according to claim 1, obtained by a method comprising the following steps:

a) introduction of an assembly (3) constituted of a biopolymer membrane (4) comprised between two cellulose sheets (A) and (B), in a vessel comprising:

a first compartment (1) and a second compartment (2), each comprising an electrode, a first electrode being an anode placed in the first compartment (1) and a second electrode being a cathode placed in the second compartment (2), the walls of the first compartment (1) and the second compartment (2) brought into contact with one another each having an opening placing in communication the first and the second compartments, the assembly (3) being arranged in said opening between the first and the second compartments in such a way as to close it, the cellulose sheet (A) being on the side of the first compartment (1) and the cellulose sheet (B) on the side of the second compartment (2), b) filling the first compartment (1) with an aqueous solution containing at least one cation chosen from: calcium ions, silver ions, zinc ions, copper ions, sodium ions, magnesium ions and aluminium ions, and the second compartment (2) with an aqueous solution containing at least one anion chosen from fluoride ions, sulphate ions, carbonate ions, silicate ions and phosphate ions;

c) application of an electrical voltage between the electrodes;

d) turning over the assembly (3) in such a way that the cellulose sheet (A) is on the side of the second compartment and the cellulose sheet (B) on the side of the first compartment, or exchange of the solutions and electrodes of the first and the second compartments;

c') application of an electrical voltage between the electrodes, said voltage being equal to that applied at step (c) and being applied for a duration identical to that of step (c);

e) removal and rinsing of the assembly (3);

f) recovery and drying of the mineralised biopolymer membrane.

4. The biopolymer membrane according to claim 3, wherein it is a collagen membrane, an alginate membrane or a chitosan membrane.

5. The biopolymer membrane according to claim 3, wherein the aqueous solution placed in the first compartment (1) contains at least calcium ions, and the aqueous solution placed in the second compartment (2) contains at least phosphate ions.

6. The biopolymer membrane according to claim 3, wherein during steps (c) and (c'), the electrical voltage applied is comprised between 2 to 13 Volts.

7. The biopolymer membrane according to claim 3, wherein step (c) of application of an electrical voltage lasts from 8 to 16 hours.

8. The biopolymer membrane according to claim 3, wherein during steps (c) and (c'), the aqueous solution containing at least one cation is stirred continuously.

9. The biopolymer membrane according to claim 3, wherein during steps (c) and (c'), the aqueous solution containing at least one cation is saturated with cations by a continuous addition of a hydroxide of said cation.

10. The biopolymer membrane according to claim 3, wherein the pH of the aqueous solution containing at least one anion is comprised between 7 and 11.

11. The biopolymer membrane according to claim 3, wherein step (f) of drying the mineralised biopolymer membrane is carried out at a temperature below 35° C.

12. A method for producing a biopolymer membrane mineralised on its faces according to claim 1, comprising the following steps:

a) introduction of an assembly (3) constituted of a biopolymer membrane (4) comprised between two cellulose sheets (A) and (B), in a vessel comprising:

a first compartment (1) and a second compartment (2), each comprising an electrode, a first electrode being an anode placed in the first compartment (1) and a second electrode being a cathode placed in the second compartment (2), the walls of the first compartment (1) and the second compartment (2) brought into contact with one another each having an opening placing in communication the first and the second compartments, the assembly (3) being arranged in said opening between the first and the second compartments in such a way as to close it, the cellulose sheet (A) being on the side of the first compartment (1) and the cellulose sheet (B) on the side of the second compartment (2), b) filling the first compartment (1) with an aqueous solution containing at least one cation chosen from: calcium ions, silver ions, zinc ions, copper ions, sodium ions, magnesium ions and aluminium ions, and the second compartment (2) with an aqueous solution containing at least one anion chosen from fluoride ions, sulphate ions, carbonate ions, silicate ions and phosphate ions;

c) application of an electrical voltage between the electrodes;

d) turning over the assembly (3) in such a way that the cellulose sheet (A) is on the side of the second compartment and the cellulose sheet (B) on the side of the first compartment, or exchange of the solutions and electrodes of the first and the second compartments;

c') application of an electrical voltage between the electrodes, said voltage being equal to that applied at step (c) and being applied for a duration identical to that of step (c);

e) removal and rinsing of the assembly (3);

f) recovery and drying of the mineralised biopolymer membrane.

13. The method according to claim 12, wherein the biopolymer membrane is a collagen membrane, an alginate membrane or a chitosan membrane.

14. The method according to claim 12, wherein the aqueous solution placed in the first compartment (1) contains at least calcium ions, and the aqueous solution placed in the second compartment (2) contains at least phosphate ions.

15. The method according to claim 12, wherein during steps (c) and (c'), the electrical voltage applied is comprised between 2 to 13 Volts.

16. The method according to claim 12, wherein step (c) of application of an electrical voltage lasts from 8 to 16 hours.

17. The method according to claim 12, wherein during steps (c) and (c'), the aqueous solution containing at least one cation is stirred continuously.

18. The method according to claim 12, wherein during steps (c) and (c'), the aqueous solution containing at least one cation is saturated with cations by a continuous addition of a hydroxide of said cation.

19. The method according to claim 12, wherein the pH of the aqueous solution containing at least one anion is comprised between 7 and 11.

20. The method according to claim 12, wherein step (f) of drying the mineralised biopolymer membrane is carried out at a temperature below 35° C.

* * * * *